United States Patent [19]
Booker

[11] Patent Number: 5,332,550
[45] Date of Patent: Jul. 26, 1994

[54] AEROSOL SAMPLER

[75] Inventor: David R. Booker, Weymouth, United Kingdom

[73] Assignee: United Kingdom Atomic Energy Authority, Harwell, United Kingdom

[21] Appl. No.: 100,440

[22] Filed: Aug. 2, 1993

[30] Foreign Application Priority Data

Sep. 1, 1992 [GB] United Kingdom ............... 9218659

[51] Int. Cl.$^5$ .............................................. G01G 3/14
[52] U.S. Cl. .................................. 422/83; 422/101; 422/120; 422/121; 422/128; 73/32 A; 73/28.01; 73/863.21
[58] Field of Search ............... 422/83, 101, 128, 120, 422/121; 73/32 A, 28.01, 863.21, 863.22, 863.23

[56] References Cited

U.S. PATENT DOCUMENTS

| | | | |
|---|---|---|---|
| 3,901,798 | 8/1975 | Peterson | 209/143 |
| 3,926,271 | 12/1975 | Patashnick | 177/210 |
| 4,074,562 | 2/1978 | North | 73/32 A |
| 4,092,845 | 6/1978 | Prodi et al. | 73/28 |
| 4,391,338 | 7/1983 | Patashnick et al. | 177/210 |
| 4,461,183 | 7/1984 | Wedding | 73/863.21 |
| 4,568,190 | 2/1986 | Carlon et al. | 356/439 |
| 4,640,140 | 2/1987 | Burghoffer et al. | 73/863.22 |
| 4,649,760 | 3/1987 | Wedding | 73/863.23 |
| 4,651,285 | 3/1987 | Collins et al. | 364/496 |
| 4,696,181 | 9/1987 | Rupprecht et al. | 73/580 |
| 4,764,186 | 8/1988 | Langer | 55/17 |
| 4,827,746 | 5/1989 | Kawaguchi | 73/32 A |
| 4,941,899 | 7/1990 | Liu | 55/270 |
| 5,006,227 | 4/1991 | Behm et al. | 209/143 |

Primary Examiner—James C. Housel
Assistant Examiner—Harold Y. Pyon
Attorney, Agent, or Firm—William R. Hinds

[57] ABSTRACT

An aerosol sampler comprises at least one U-tube whose ends are fixed to a support, and through which the aerosol is caused to flow. Means are provided to set the tube vibrating, and to measure its resonant frequency. The bend of the U-tube acts as an impactor so aerosol particles larger than a cut-off size are trapped, causing a change in the measured frequency. A sampler may include a number of such U-tubes in series, with steadily decreasing cut-off sizes, so the aerosol particulate size distribution can be determined.

11 Claims, 2 Drawing Sheets

AEROSOL SAMPLER

This invention relates to an aerosol sampler, and to a method of sampling an aerosol, for example for providing an indication of the concentration of aerosol particulates, in particular the concentrations of particulates in different size ranges.

An aerosol comprises a gas in which are dispersed particulates, which may be either solid particles or liquid droplets.

According to the present invention there is provided an aerosol sampler comprising support means, at least one U-tube whose ends are fixed to the support means, means for causing an aerosol to flow continuously through the U-tube, means for causing the U-tube to vibrate, and means for detecting the resonant frequency of the U-tube, means for measuring the rate of change of the resonant frequency, and means for determining from the rate of change of resonant frequency the rate at which aerosol particulates are deposited within the U-tube.

In this specification the term U-tube refers to a tube comprising substantially straight inlet and outlet portions linked by a bent portion; the exact shape of the tube is not of significance, and it may be of non-uniform bore. The bend of the U-tube acts as an impactor, that is to say it imposes a change on the flow direction of the aerosol so smaller particulates are carried along with the diverted gas flow whereas larger particulates (due to their inertia) impact with the wall of the tube. The cut-off size (that is to say the size of particulate for which the proportion of particulates which undergoes impaction is a half) for such a U-tube impactor depends on the radius of curvature of the bend, and also depends on the nature of the flow which may be characterized by the Reynolds' Number and the Stokes' Number. For a given flow rate, the diameter of the tube determines the Reynolds' Number, while the bend radius can be chosen to provide a desired cut-off size.

Preferably the sampler comprises a plurality of such U-tubes arranged so the flows through the U-tubes are in series, the cut-off size provided by each U-tube after the first being less than that of the preceding U-tube in the series, and each U-tube being provided with means to cause it to vibrate, and means to detect its resonant frequency.

The resonant frequency of such a U-tube depends upon the elastic properties of the material of which it made, and on the vibrating mass, that is the mass of the tube, the gas, the gas-borne aerosol particulates, and of the impacted aerosol particulates which remain on the wall of the tube. At constant temperature the mass of gas is typically constant; while that of the gas-borne particulates is typically much less than that of the impacted particulates. Hence measurement of the rate of change of the resonant frequency enables the rate of trapping of aerosol particulates by that impactor U-tube to be determined. If it can be assumed that all particulates which undergo impaction remain trapped, then such a multi-U-tube sampler enables the concentration to be calculated of aerosol particulates in each of the size categories set by the cut-off sizes provided by the successive U-tubes. This assumption is usually valid for aerosols of liquid droplets, whereas for some aerosols of solid particles it may be necessary to coat the inner walls of the U-tubes to ensure the particles undergoing impaction remain trapped.

Means may also be provided to change the aerosol flow rate through the U-tube or U-tubes. This changes the cut-off size provided by each tube, and so changes the size resolution of the sampler. In addition, means may also be provided to enable the particulate re-entrainment characteristics of a sampled aerosol to be assessed. This can be achieved by monitoring any changes in the resonant frequency which occur when there is a flow of gas, but with a filter arranged at the inlet to the sampler to trap all the particulates.

The sampler may comprise additional means in association with one or more of the U-tubes to provide desired cut-off characteristics. For example within a U-tube may be provided means to define an aperture upstream of a plate, to give a desired cut-off size less than is conveniently obtainable from the bend radius. The particulate trapping may take place by a mechanism other than inertial impaction, for example electrostatic means may be provided to enhance the trapping of particulates by one or more of the U-tubes. Furthermore the sampler may also include a filter to remove substantially all aerosol particulates from the gas stream. Such a filter may be provided in one of the U-tubes; alternatively it may be provided in the support. The sampler may also comprise a further U-tube downstream of such a filter, with a vibration-causing means and frequency detection means. The resonant frequency of this U-tube enables the density of the gas (in the absence of particulates) to be measured.

Where there are a plurality of U-tubes, means must be provided to ensure communication between an end of one U-tube and an end of the next U-tube in the series. Preferably the U-tubes are arranged so the communicating ends of successive U-tubes are aligned with each other. The U-tubes may all be fixed to a common support means, and in this case ducts may be defined within the support means to provide the requisite communication. Since particulate deposition onto a straight portion of a tube is much less than that onto a bend, and since the ducts within the support means can be of the same or greater bore than the U-tubes but also much shorter, wall losses can be negligible. The ducts between ends of successive U-tubes may incorporate three-way valves, so individual U-tubes can be purged, or so aerosol deposited in an individual U-tube may be chemically analyzed.

The invention also provides a method of sampling an aerosol in which the aerosol is caused to flow through one or more U-tubes in series, the U-tubes are caused to vibrate, and for the or each tube the resonant frequency is monitored, the rate of change of the resonant frequency is measured, and hence the rate of deposition of aerosol particulates within the U-tube is determined.

BRIEF DESCRIPTION OF THE DRAWINGS

The invention will now be further described, by way of example only, and with reference to the accompanying drawings in which:

Referring to FIG. 1 an aerosol sampler 10 comprises a chamber 12 which may be evacuated during operation. Within the chamber 12 is a rigid stainless steel support bar 14, and fixed to the bar 14 are nine U-tubes 16–24 all of 2 mm bore quartz glass tube. The U-tubes 16–24 are arranged so a gas can flow through them in series, successive U-tubes being on opposite sides of the bar 14 with their ends aligned, and communicating via ducts 26 through the bar 14, also of 2 mm bore. Each duct 26 incorporates a three-way valve 28 (two of which are shown diagrammatically) so that individual U-tubes can instead be put into communication with side tubes 30. A gas or an aerosol can flow into the first U-tube 16 of the series through an inlet tube 32; an outlet tube 34 communicates with the last U-tube 24 of the series, and is connected to a pump 36 which causes gas or aerosol to flow through all the U-tubes 16–24.

Figure 1:
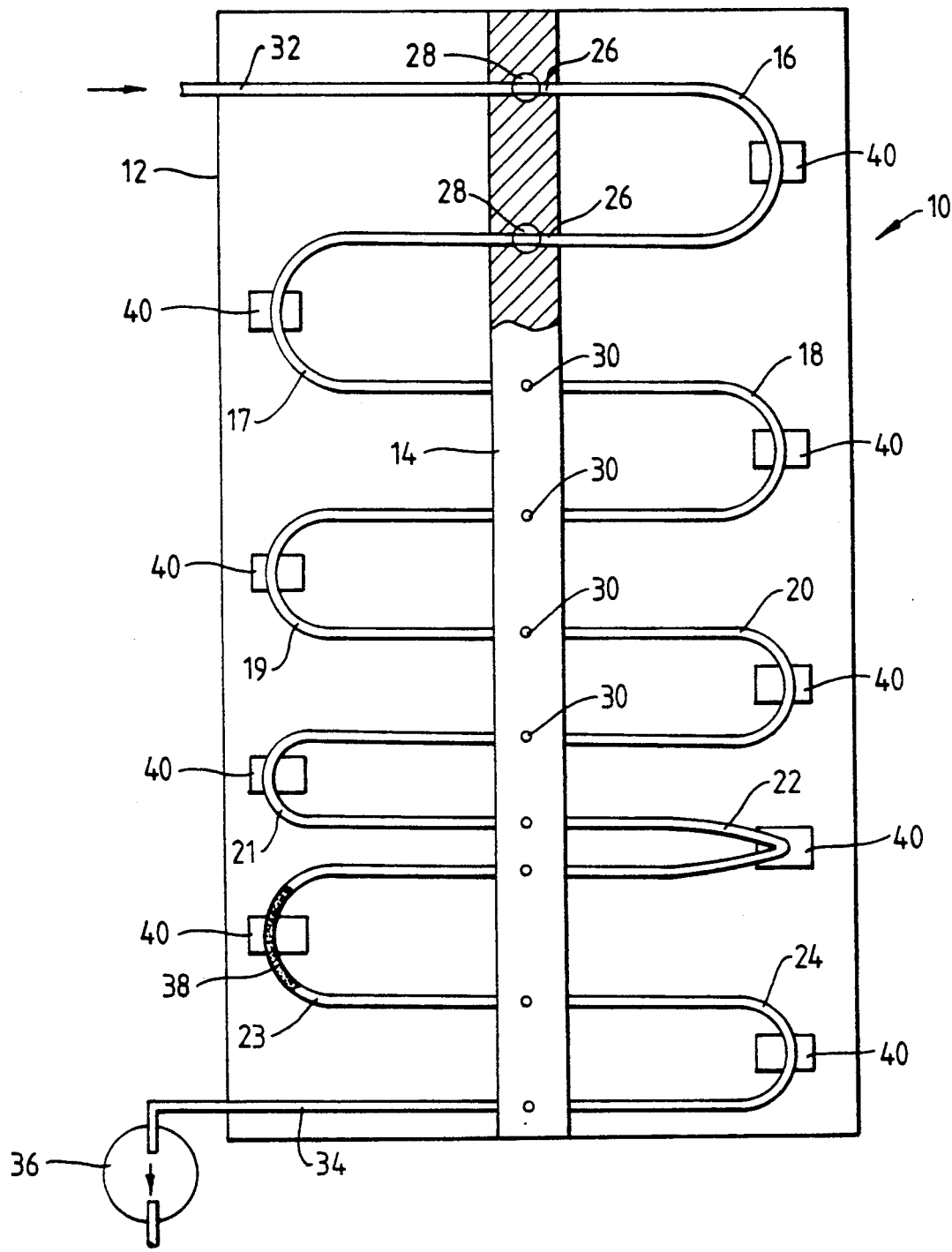
FIG. 1 shows an aerosol sampler, partly in section, and partly diagrammatically.

The first U-tube 16 has the bend of largest radius of curvature; for each of the next six U-tubes 17–22 the radius of curvature of the bend is less than that of the preceding U-tube 16–21. The eighth U-type 23 has its bend filled with glass fibres as a filter 38. Consequently if an aerosol flows through the inlet tube 32, the largest particulates will undergo impaction in the bend of the first U-tube 16, and so be trapped there, while the sizes of aerosol particulates which are trapped in subsequent U-tubes are progressively less along the series. For example the first U-tube 16 might have a cut-off size of 10 micrometers, the next U-tube 17 a cut-off size of 8 micrometers, and so on, the seventh U-tube 22 having a cut-off size of 1 micrometer, and smaller particulates being trapped in the filter 38 of the eighth U-tube 23.

Adjacent to the bend of each U-tube 16–24 is an electromagnetic means 40 (shown diagrammatically) to cause the U-tube 16–24 to vibrate (out of the plane of the Figure), and to monitor its resonant frequency. For example the means 40 might include a small ceramic magnet fixed to the U-tube at the bend, and electromagnet coils above and below the magnet. Alternatively the vibration might be driven electromagnetically, while the vibration frequency is monitored by an optical sensor, so that the frequency monitoring is decoupled from the driving of the vibration. The means 40 are connected to a power supply unit (not shown), and to respective frequency meters (not shown). Alternatively the sampler 10 might include a single frequency meter to which signals from the nine means 40 are supplied in turn, for example by means of a multiplexer. Electromagnetic means 40 are known per se in relation to U-tube densitometers as described in UK Patent GB 1 189 083.

At a given temperature the effective internal volume and the elastic properties of each such U-tube are constants, and the resonant frequency f of the vibration is related to the density $\eta$ of the contents of the U-tube by:

$$f^2 = 1/A + \rho B)$$

A and B are constants which can readily be determined experimentally from measurements with two fluids of known density. The effective internal volume of the U-tube can be determined experimentally by either placing a calibration mass in the U-tube and monitoring the change in frequency, or by monitoring the frequency change as a liquid is gradually added to the U-tube. Hence each U-tube 16–24 can be calibrated so the changes in frequency f are related to the change in deposited mass of particulates, and to the location of the deposited mass.

In use, the sampler 10 is desirably held at a constant temperature, and the chamber 12 may be evacuated (to minimize damping). The pump 36 is energised to give a desired flow rate for example of 5 liters per minute. The frequency of vibration of each U-tube 16–24 is monitored, and the rate of change of frequency of each of the first eight U-tubes 16–23 enables the rate of deposition of aerosol particulates, in the size range trapped by that U-tube, to be determined. The frequency of the last U-tube 24 enables the density of the gas from which substantially all the particulates have been removed to be monitored. Hence the sampler 10 enables the concentration of aerosol particulates, and their size distribution, to be measured. These measurements can be taken within a few minutes of starting the aerosol flow, depending on the flow rate and on the aerosol concentration, because the measured frequency changes can be sensitive to as little as $10^{-8}$ g of deposited particulates.

After a measurement of the size distribution has been made, the resolution of sampler 10 can be changed and the measurements repeated by changing the aerosol flow rate (by adjusting the pump 36), as the cut-off size of each U-tube 16–22 is affected by the flow rate. The extent to which re-entrainment of deposited particulates occurs can be monitored by causing the gas flow to pass through a filter (not shown) before it flows into the inlet tube 32; any changes in the resonant frequencies under these circumstances indicate that deposited particulates are being re-entrained (or are evaporating). If desired, the deposited particulates in one or more of the U-tubes 16–23 can be subsequently washed out, for example for analysis, using the valves 28 and the side tubes 30.

It will be appreciated that an aerosol sampler of the invention may differ in several ways from that of FIG. 1. For example the number of U-tubes might be different, for example ten or twelve. Where a portable sampler is required and size resolution is not important, a sampler might have only two or three U-tubes.

Figure 2:
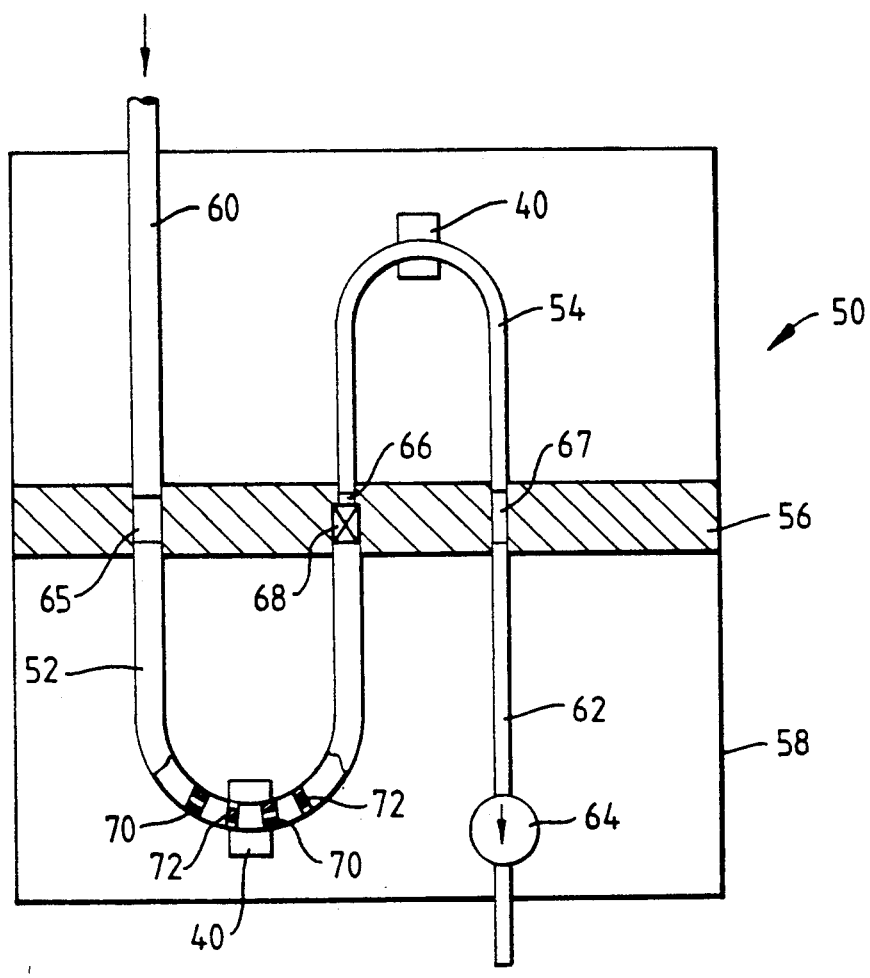
FIG. 2 shows an alternative aerosol sampler, partly diagrammatically.

Referring now to FIG. 2 there is shown an alternative, portable, aerosol sampler 50. The sampler 50 comprises a first U-tube 52 of 4 mm bore quartz glass in series with a second U-tube 54, of 2 mm bore quartz glass. The U-tubes 52 and 54 are fixed to opposite sides of a support bar 56 in an evacuatable enclosure 58. A 4 mm bore inlet tube 60 communicates with the first U-tube 52, while a 2 mm bore outlet tube 62 incorporating a pump 64 communicates with the second U-tube 54. The tubes 60, 52, 54 and 62 are in series, and communicate via ducts 65, 66, 67 through the support bar 56. Within the duct 66 between the first and the second U-tubes 52, 54 is a filter 68.

In the bend of the first U-tube 52 are two aperture/plate impactors in series, each comprising a ring 70 defining a 1.5 mm aperture, 4 mm upstream of a 2.5 mm diameter plate 72 supported by radial arms. Such an impactor provides a smaller cut-off size than can conveniently be achieved using a bent tube. The cut-off size, d, has been found to be given by:

$$d = K(pD/V)^{\frac{1}{2}}$$

where
$p = 3.24 \times 10^{-7}$ m$^2$/s (assuming the gas is air)
D = diameter of air jet from the aperture
V = velocity of air jet at the centre
and K is a dimensionless constant determined by the cross-sectional shape of the jet and by the ratio of the aperture-to-plate spacing to D. If this ratio is 3 the value of K is 0.38 for a circular jet. (This distance ratio is desirably between 0.35 and 10, preferably between 1 and 4; the larger this ratio the less sharp is the cut-off between those particulate sizes which undergo impaction and those which do not, and K becomes slightly larger. The parameter p is in fact given by 18 times the coefficient of viscosity of air divided by the product of the density of the particulate material and a slip factor which is just above one for particulates greater than a micron in diameter). Hence the cut-off size imposed by the aperture/plate impactor 70,72 with an air flow rate of 1 liter/min would be about 2.7 micrometers.

As in the sampler 10 of FIG. 1, electromagnetic and optical means 40 are provided adjacent to the bend of each U-tube 52, 54 so the U-tubes can be caused to vibrate, and so the resonant frequency of each can be measured.

In use, with the pump 64 operating, the rate of change of the resonant frequency of the first U-tube 52 enables the concentration to be measured of aerosol particulates larger than the cut-off size imposed by the two aperture/plate impactors 70, 72. Substantially all smaller particulates in the aerosol stream entering the inlet tube 60 will be trapped by the filter 68. Hence the frequency of the second U-tube 54 enables the density of the gas stream to be measured. This enables compensation to be made for any changes in gas density.

I claim:

1. An aerosol sampler comprising support means, at least one U-tube whose ends are fixed to the support means, means for causing an aerosol to flow continuously through the U-tube, means for causing the U-tube to vibrate, means for detecting the resonant frequency of the U-tube, means for measuring the rate of change of the resonant frequency, and means for determining from the rate of change of resonant frequency the rate at which aerosol particulates are deposited within the U-tube.

2. An aerosol sampler as claimed in claim 1 comprising a plurality of such U-tubes arranged so the flows through the U-tubes are in series, the U-tubes being such that each U-tube after the first provides a smaller cut-off size than that of the preceding U-tube in the series, and each U-tube being provided with means causing it to vibrate, means for detecting its resonant frequency, for measuring the rate of change of the resonant frequency, and for determining the rate of deposition of aerosol particulates.

3. An aerosol sampler as claimed in claim 2 wherein the U-tubes are all fixed to a common support means, and ducts are defined within the support means to provide communication between successive U-tubes in the series.

4. An aerosol sampler as claimed in claim 3 additionally comprising three-way valves in the ducts between successive U-tubes.

5. An aerosol sampler as claimed in claim 1 also comprising means to change the flow rate through the or each U-tube, so as to change the sizes of particulates deposited in the or each tube, and so change the size resolution of the sampler.

6. An aerosol sampler as claimed in claim 1 wherein at least one U-tube incorporates additional means to reduce the sizes of particulates deposited therein.

7. An aerosol sampler as claimed in claim 6 wherein the additional means comprises, within a said U-tube, an impactor plate, and means to define an aperture upstream of the impactor plate.

8. An aerosol sampler as claimed in claim 6 wherein the additional means comprises a filter medium.

9. An aerosol sampler as claimed in claim 1 also comprising a filter unit, and a further U-tube downstream of the filter unit, with a vibration-causing means and frequency detection means, whereby the density of the gas in the absence of aerosol particulates can be monitored.

10. A method of sampling an aerosol in which the aerosol is caused to flow through one or more U-tubes in series, the U-tubes are caused to vibrate, and for the or each tube the resonant frequency is monitored, the rate of change of the resonant frequency is measured, and hence the rate of deposition of aerosol particulates within the U-tube is determined.

11. An aerosol sampler as claimed in claim 1 also comprising a filter medium located in the flow downstream of the or the first U-tube.

* * * * *